(12) United States Patent  
Geisler et al.

(10) Patent No.: US 7,195,614 B2  
(45) Date of Patent: Mar. 27, 2007

(54) METHODS AND APPARATUS FOR INTRAOPERATIVE ADMINISTRATION OF ANALGESIA

(75) Inventors: Fred H. Geisler, Aurora, IL (US); Dan L. Becker, Orlando, FL (US)

(73) Assignee: Spinal Integration, LLC, Windermere, FL (US)

( * ) Notice: Subject to any disclaimer, the term of this patent is extended or adjusted under 35 U.S.C. 154(b) by 89 days.

(21) Appl. No.: 11/042,489

(22) Filed: Jan. 25, 2005

(65) Prior Publication Data

US 2006/0167436 A1   Jul. 27, 2006

(51) Int. Cl.  
*A61M 31/00* (2006.01)

(52) U.S. Cl. .................................. 604/170.01

(58) Field of Classification Search ............... 604/161, 604/500, 506–8, 510, 512, 158, 160, 164.01, 604/164.03, 170.01, 170.02, 170.03, 507, 604/508; 264/162, 285, 292, 296; 606/108  
See application file for complete search history.

(56) References Cited

U.S. PATENT DOCUMENTS

| | | | | |
|---|---|---|---|---|
| 3,610,239 A | * | 10/1971 | Huggins | ..................... 604/161 |
| 4,518,383 A | * | 5/1985 | Evans | ......................... 604/512 |
| 4,721,506 A | * | 1/1988 | Teves | ......................... 604/506 |
| 5,171,226 A | * | 12/1992 | McCrory | ............... 604/164.01 |
| 5,871,470 A | * | 2/1999 | McWha | ....................... 604/158 |
| 6,027,480 A | * | 2/2000 | Davis et al. | ........... 604/164.05 |
| 6,261,582 B1 | | 7/2001 | Needham et al. | |
| 6,558,390 B2 | | 5/2003 | Cragg | |
| 6,733,496 B2 | | 5/2004 | Sharkey et al. | |
| 6,736,835 B2 | | 5/2004 | Pellegrino et al. | |
| 6,769,546 B2 | * | 8/2004 | Busch | ......................... 206/571 |
| 2005/0070919 A1 | * | 3/2005 | Lieberman | .................. 606/108 |

* cited by examiner

*Primary Examiner*—Anhtuan T. Nguyen  
*Assistant Examiner*—Laura Bouchelle  
(74) *Attorney, Agent, or Firm*—Timothy H. Van Dyke; David G. Maire; Beusse Wolter Sanks Mora & Maire, P.A.

(57) ABSTRACT

Disclosed herein is a catheter placement apparatus 900 for assisting in the placement of a catheter for administering analgesia intraoperatively in conjunction with spinal and other surgeries. The catheter placement apparatus 900 comprises a guide conduit 903 having a proximal end 904 and a distal end 906. The guide conduit 903 comprises an elongated portion 905 and a delivery arm portion 907 with a bend 935 forming the transition from the elongated portion 905 to the delivery arm portion 907. The elongated portion comprises a first conduit component 910 that is slidingly attachable to a second conduit component 915.

5 Claims, 7 Drawing Sheets

METHODS AND APPARATUS FOR INTRAOPERATIVE ADMINISTRATION OF ANALGESIA

BACKGROUND OF THE INVENTION

When patients emerge from general anesthesia after a lumbar spinal procedure they often go into lumbar muscle spasms as a result of the incisional pain combined with the abrupt loss of effective lumbar analgesia. This combination often leads to the creation of a pain spasm cycle of the lumbar muscles at the incisional wound area where the local muscle spasms cause more incisional area pain, which then cause more local muscle spasms and even more pain. Often intravenous narcotics and benzodiazepines are required to break this cycle which can last from thirty minutes to hours and in severe cases even days. This pain spasm cycle is not only quite uncomfortable to the patient but additionally prevent many patients with a smaller procedure such as a discectomy or laminoforaminotomy (typically the L4-L5 or L5-S1 level and occasionally the L3-L4 level) from going home on the day of surgery. Although, the true cost of a patient staying an extra day varies wildly depending on the region and insurance contract with the hospital, it is fair to assess the true cost in the $1000.00 to $2000.00 range. Thus there is an obvious advantage to insuring that the patients are comfortable with good pain control so that they can go home as same day surgery. The current therapy of a combination of intravenous and oral medication in the postoperative period have proven unable to prevent the incisional area pain and/or leg pain from triggering the pain spasm cycle in the majority of patients.

Three types intraoperative locally applied analgesia are available that could be implemented in an effort to prevent this pain spasm cycle:

1. Local can be Injected into the Muscle and Skin. An injection of ¼% Sensorcaine injected into the skin only just prior to skin closure in addition to before the initial skin incision carries no risk of intradural injection while providing a level of incisional analgesia. However, this superficial analgesia usually only provides incomplete pain management because the deep wound musculature structures nor the ligaments around the facet joint and posterior longitudinal ligament are not covered by the superficial injection in the skin. These deep structures cannot be adequately injected without risk of intradural injection. An intradural injection can result in various medical problems including life threatening seizures and reversible paralysis sometimes requiring a ventilator for temporary support. An intradural injection will insure that the patient will not be discharged on the day of such an injection. Additionally the total muscle that is surgically injured (painful in the postoperative period) is not only the muscle disconnected for the bone visually seen in the surgical incision but all the muscle stretched for the necessary surgical retraction. This stretch injured muscle tissue can be over 2 inches from the surgical wound and hence difficult to completely block with a local injection. The vast majority of Spinal Surgeons have been ineffective in using this form of postoperative pain management.

2. Spinal anesthesia (antrathecal). If a spinal injection is done in or near the operative site, there is always a risk of spinal fluid leak into the surgical defect. This can lead to a post operative meningocele with the spinal fluid filling the surgical area. If this occurs chronic pain or additional operation(s) may be needed. If the spinal fluid leaked through the skin then meningitis with the risk of death can occur. Spinal anesthesia is clinically utilized for intraoperative anesthesia such as child birth and hip surgery. A separate puncture remote to the lumbar surgical incision has not been routinely used for postoperative pain management in an outpatient setting because of the risk of respiratory depression on a delayed basis.

3. epidural analgesia. An epidural anesthesia administered near the L1 to T10 area provides good anesthetic coverage of both lower extremities and the low back incisional region. This is the location of the spinal cord conus were the motor and sensory nerves to the legs connect to the central nervous system and anesthetic agents are most potent in pain relief for the legs and low back area. A combination of 2 cc's of Fentanyl (100 mcg.) and 8 cc of ¼% plain preservative-free Sensorcaine is just below a motor block and allows the patient to wake up pain free. The Fentanyl is believed to have a physiologic half-life of 1 to 2 hours and hence is not a threat for delayed respiratory depression as the longer acting narcotic morphine is known to occur in some cases. This epidural analgesia is typically supplemented with an addition injection of ¼% Sensorcaine into the skin just prior to skin closure in addition to before the initial skin incision. A patch of Fentanyl 50 mcg is placed on the skin and removed in three days. Oral medication as needed on a daily basis. NSAID medications are utilized preoperatively and postoperatively as per the surgeon's routine and the clinical situation.

Of the three extra analgesia options listed above, epidural analgesia uniquely provides the promise of completely blocking the onset of the pain spasm cycle following emergence form endotracheal anesthesia after the lumbar spinal surgeries while having an extremity low incidence of estimated side effects or additional surgical complications. However, epidural administration of analgesia via the lower lumbar surgical exposure after minimally invasive lumbar spine surgical procedures does present several technique challenges. Threading an epidural catheter intra-operatively in via the small lumbar incision to the L1 to T10 region is difficult even with a guide wire. Although the surgical identification of the epidural space is obvious intraoperatively, the catheter is threaded in a path that is at right angle to the surgical vision axis making it mechanically difficult to thread with the right angle bend necessary at the bottom of the wound. Ideal catheter position is to advance the tip of the catheter into the epidural space in the midline dorsal to the thecal sac 3 to 5 inches cephalad to the operative site (to the anatomic bony level between L1 to T10). The midline dorsal location is desired since there is usually a fat pad, and hence potential space, in this location along the whole spinal axis allowing an easy path for the catheter to be threaded. If the catheter path falls off the dorsal midline to one side of the spinal canal then the cephalad passage of the catheter is restricted or blocked by the laterally exiting nerve roots. Although it is possible to use an expensive CSF lumbar drainage catheter and advance it into this midline dorsal epidural space with a bayonet forceps, this technique is very cumbersome, technically demanding, time consumining, and requires extra midline bone removal. Also in some cases it is impossible to thread the catheter especially in the small minimally invasive lumbar spinal wounds.

The threading difficulty of the epidural catheter via a lumbar surgical wound arises from the need to thread the catheter at the bottom of the wound at an essentially right angle to the line of sight of the small surgical wound. The sharp angle of turn at the bottom of the wound combined with the catheter threading is beyond the surgical capability or patience of most spinal surgeons when current supplies and equipment are utilized. Thus, there is a need for a specialized system to aid the spinal surgeon in the rapid and reliable epidural catheter placement.

BRIEF DESCRIPTION OF THE DRAWINGS

FIG. 5 is a schematic of an analgesia delivery method embodiment of the subject invention.

FIG. 6 shows a catheter placement apparatus embodiment of the subject invention.

FIG. 7 shows a catheter placment apparatus embodiment of the subject invention.

FIG. 8 shows a catheter placement apparatus embodiment of the subject invention.

DETAILED DESCRIPTION

The subject invention relates to novel apparatuses and kits, as well as methods of using same, for the delivery of analgesia intraoperatively during spine surgeries. In one embodiment, the subject invention pertains to a guide conduit for assisting placement of a catheter in a surgical site. The guide conduit comprises an elongated portion and a delivery arm portion integrated with or attached to said elongated portion.

In a specific embodiment, the invention is directed to a guide conduit comprising an elongated portion and a delivery arm portion integrated with or attached to said elongated portion, wherein the longitudinal axis of the elongated portion and the longitudinal axis of the delivery arm portion form an angle of from about 50 degrees to about 170 degrees. The elongated portion defines a substantially enclosed channel for keeping the catheter in place as it is directed by the conduit to the surgical site and on to the target site for administering the analgesia. The delivery arm portion may be substantially enclosed as well.

Furthermore, in alternative embodiments, the elongated portion may be comprised of two or more parts that are disengageable such that in an engaged form they define a substantially enclosed channel and in a disengaged form the substantially enclosed channel is opened. Upon placement of the catheter in the desired location proximal to the surgical site, the two or more parts are disengaged thereby facilitating an easier removal of the conduit from the surgical site without disrupting the placement of the catheter. The delivery arm portion need not be enclosed or substantially enclosed but rather need only define a channel with walls sufficient to hold and control the catheter. In embodiments wherein the elongated portion is comprised of two or more disengageable parts, the delivery arm portion typically comprises a substantially open region to allow the facile removal of the guide conduit away from the catheter sitting in the elongated body portion and delivery arm portion out of the guide conduit.

In another embodiment, the subject invention pertains to a method for intraoperatively administering analgesia at a predetermined target site in a patient. The method involves creating a surgical site, conducting the appropriate surgery to address the patient's need, and inserting a guide conduit into the surgical site, wherein the guide conduit comprises an elongated portion and a delivery arm portion integrated with or attached to said elongated portion. The elongated portion is cannulated to define a substantially enclosed channel. A catheter is passed through the conduit and out its distal end such that it extends out of the conduit and is positioned at the target site. Analgesia is delivered to the target site through the catheter.

In a further embodiment, the subject invention is directed to a method for intraoperatively administering analgesia at a predetermined target site in a patient. The method comprises creating a surgical site; inserting a guide conduit into said surgical site, said guide conduit comprising an elongated portion comprising a first component and a second component, wherein said first and second component are removably attachable to each other; and a delivery arm portion integrated with or attached to said second component. In one embodiment, the axis of said second component and the axis of said delivery arm portion form an angle of from about 30 degrees to about 120 degrees, and wherein said first and second components are configured to define a substantially enclosed channel into which a catheter is directed; passing a catheter comprising a distal end and a proximal end, through said guide embodiment such that said distal end of said catheter extends out of said conduit and is positioned at said target site; disengaging said first component from said second component; removing said first and second components from said surgical site; closing said surgical site up to the subcutaneous layer of said patient while leaving said catheter in said patient; directing analgesia through said catheter and out said distal end of said catheter thereby delivering analgesia to said target site; removing said catheter from said patient; and closing said subcutaneous layer. The term removably attachable may include two parts that no longer contact each other, or merely move in a way as to open the substantially enclosed channel.

Figure 1:
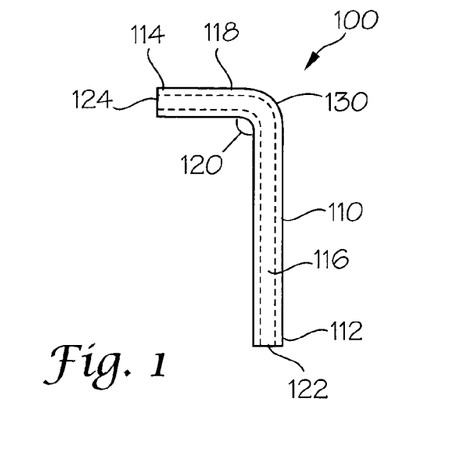
FIG. 1 shows a side view of a guide conduit embodiment of the subject invention.

Turning to the figures, FIG. 1 shows one guide conduit embodiment 100 configured to assist in the delivery of analgesia during spinal surgeries. The guide conduit 100 comprises a proximal end 112 and a distal end 114. The guide conduit comprises a bend 130 forming angle 120. Proximal to the bend 130 is an elongated body portion 110. Distal to the bend 130 is a delivery arm portion 118. The guide conduit embodiment 100 is typically designed so as to be substantially L-shaped wherein angle 120 formed by the elongated body portion 110 and delivery arm portion 118, is between about 50 degrees and 120 degrees. Guide conduit embodiment is cannulated such as to define an enclosed channel 116. Those skilled in the art will appreciated that the channel in this and the other guide conduit embodiments taught herein may be completely enclosed or substantially enclosed. As used herein, the term substantially enclosed means the channel has structure sufficient to hold the catheter in place and guide the catheter during insertion into the surgical site and on to the target site of analgesia delivery. Substantially enclosed is meant to be more inclusive than completely enclosed, but should be interpreted to include being completely enclosed. Channel 116 has a first opening 122 at the proximal end and a second opening at 124 at the distal end 114. In a specific embodiment, the angle 120 is 50 to about 120 degrees, however, the angle may range from 1 to 179 degrees. The optimal angle will be readily determined by those skilled in the art depending on the type of surgery being performed and the most common anatomical confines of the surgical area.

Figure 2:
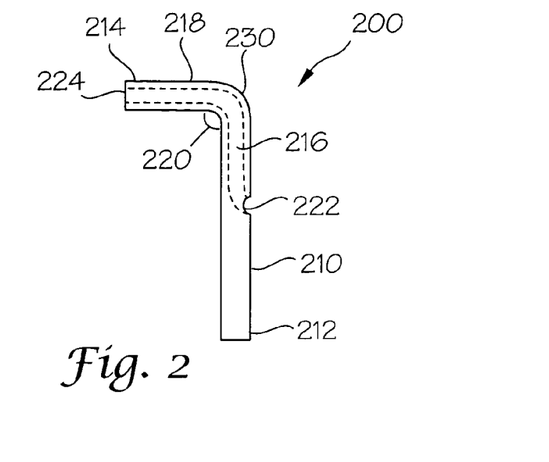
FIG. 2 shows a side view of a guide conduit embodiment of the subject invention.

An alternative embodiment for the guide conduit 200 is shown in FIG. 2. The guide conduit 200 comprises a proximal end 212 and a distal end 214. The guide conduit 200 comprises a bend 230 forming an angle 220. Proximal to the bend 230 is an elongated body portion 210. Distal to the bend 230 is a delivery arm portion 218. Like the guide conduit embodiment 100 shown in FIG. 1, the angle 220 will typically range from 50 degrees to about 120 degrees. Distal to the bend 230 is a delivery arm portion 218. Guide conduit embodiment 200 is cannulated having a channel 216. The channel 216 has a first opening 222 which opens out from the side wall of the elongated portion 210. The channel 216 has a second opening 224, which opens out the distal end 214.

Figure 3:
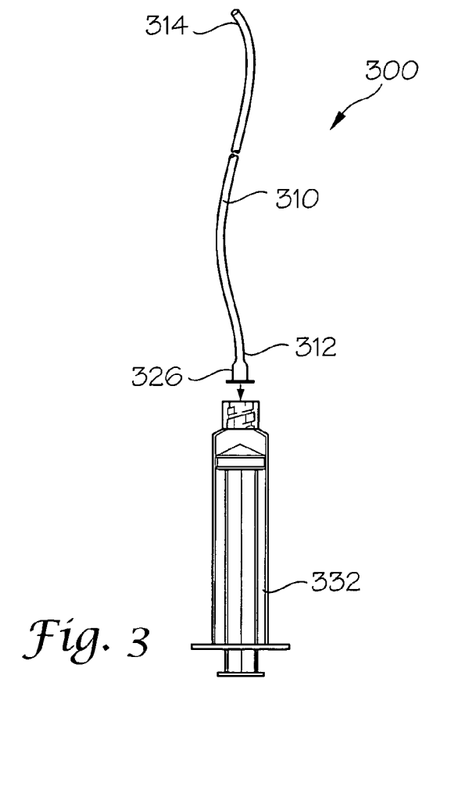
FIG. 3 shows a side view of a delivery catheter for use in accord one embodiment of the subject invention.

As described herein, it is beneficial to administer analgesia a certain loci proximal to the surgical site, typically cephalad to the surgical site. Shown in FIG. 3 is one catheter embodiment 300 suitable for delivering analgesia to a targeted area. The catheter 300 comprises an elongated portion 310 having a distal end 314 and a proximal end 312. Provided integral with or attached to the proximal end 312 is a fastening means 326. The fastening means may comprise any suitable means to attach to a container of analgesia. Examples include, but are not limited to, a snap-fit, friction-fit threaded fitting and a Luer-Lok fitting. Typically, the fastening means is a Luer-Lok, which is conventional in the art and may be readily attached to a syringe comprising an analgesic solution. Typically, disposed within the catheter is a Teflon coated guidewire, or similar guidewire, that is removable from the catheter. A Teflon coated guidewire is shown as 375 which has been removed from catheter 300. Containers containing analgesia that may be used in accord with the teachings herein include, but are not limited to, a vial, bag, pouch, or syringe. As shown in FIG. 3, the most typical embodiment for the container is a syringe 332.

Figure 4:
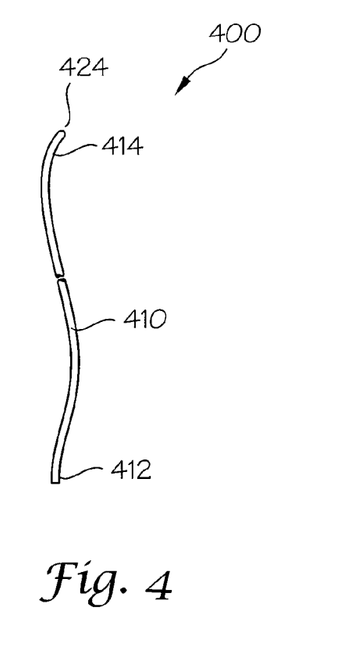
FIG. 4 shows a side view of a stylet for use in accord with one embodiment of the subject invention.

FIG. 4 shows one example of a stylet 400 that may be used in conjunction with the guide conduit embodiments primarily for the purpose of clearing out debris in the guide conduit embodiments and forming a pathway from the surgical window in which to direct the catheter 300. The stylet 400 comprises an elongated body portion 410 that comprises a proximal end 412 and a distal end 414. Preferably, the stylet comprises at its distal end a ballpoint.

Figure 5A:
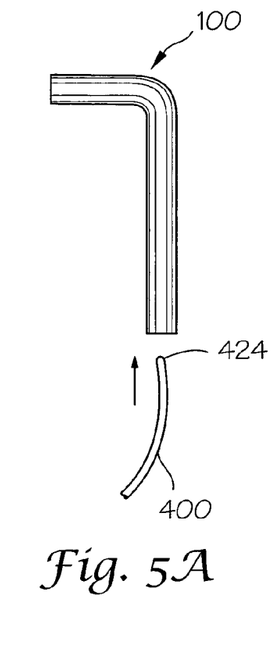
FIG. 5A–C shows placement of a guide conduit, insertion of a stylet in the guide conduit, and removal of the stylet from the guide conduit.
Figure 5B:
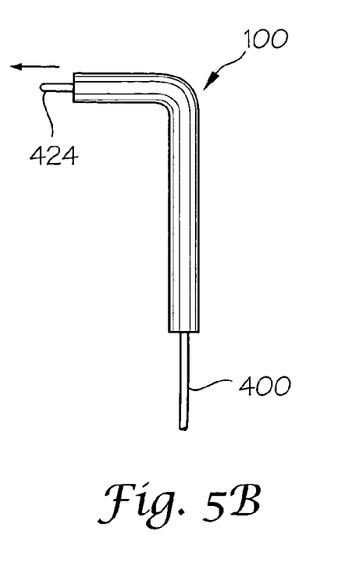
Figure 5C:
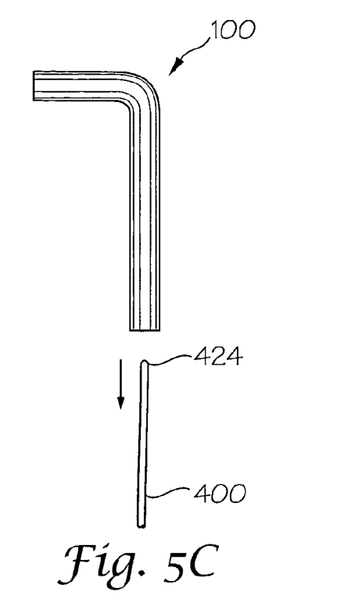
Figure 5D:
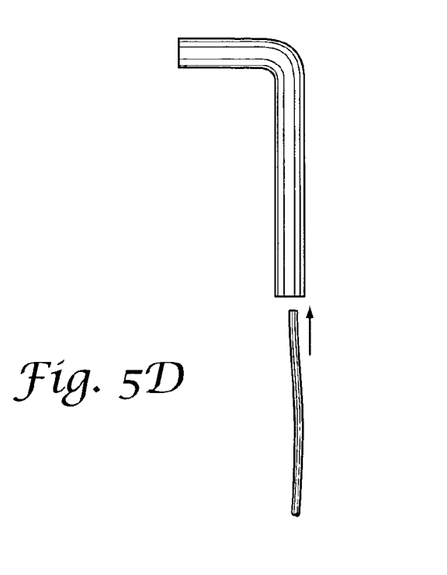
FIG. 5D–E shows insertion of a catheter into the guide conduit and delivery of analgesia.
Figure 5E:
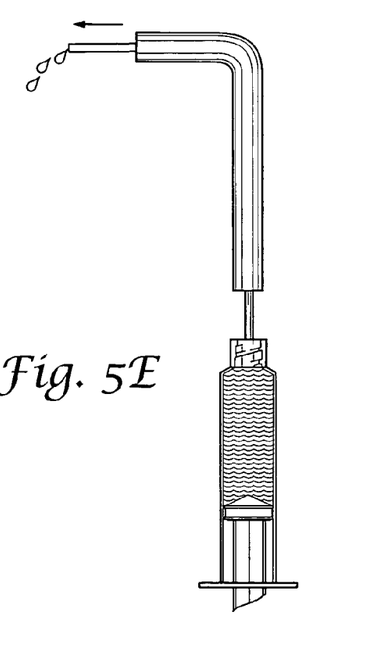

One method embodiment for administering analgesia at a targeted site in a patient comprises implementing the guide conduit embodiment 100 the stylet 400 and the catheter 300. Turning to FIG. 5A, the physician properly aligns the guide conduit embodiment 100 at the surgical window such that the distal end 114 points to the targeted site for analgesia administration. The physician inserts the stylet 400 with the ballpoint end 424 through the guide conduit embodiment 100 such that it projects out the distal end 114 of the guide conduit 100. (See FIG. 5B) The stylet is pushed through the patient's tissue to form a pathway for the catheter. The stylet 400 is removed from the guide conduit 100 (see FIG. 5C) and then the catheter 300 is inserted through the guide conduit 100 distal end 314 first. (FIG. 5D). The catheter 300 is pushed through the guide conduit such that is projects out of the guide conduit embodiment 100 and through the pathway (not shown) previously formed by the stylet 400. Once the catheter is in place, analgesia is delivered to the targeted region (see FIG. 5E).

Figures 6A, 6B:
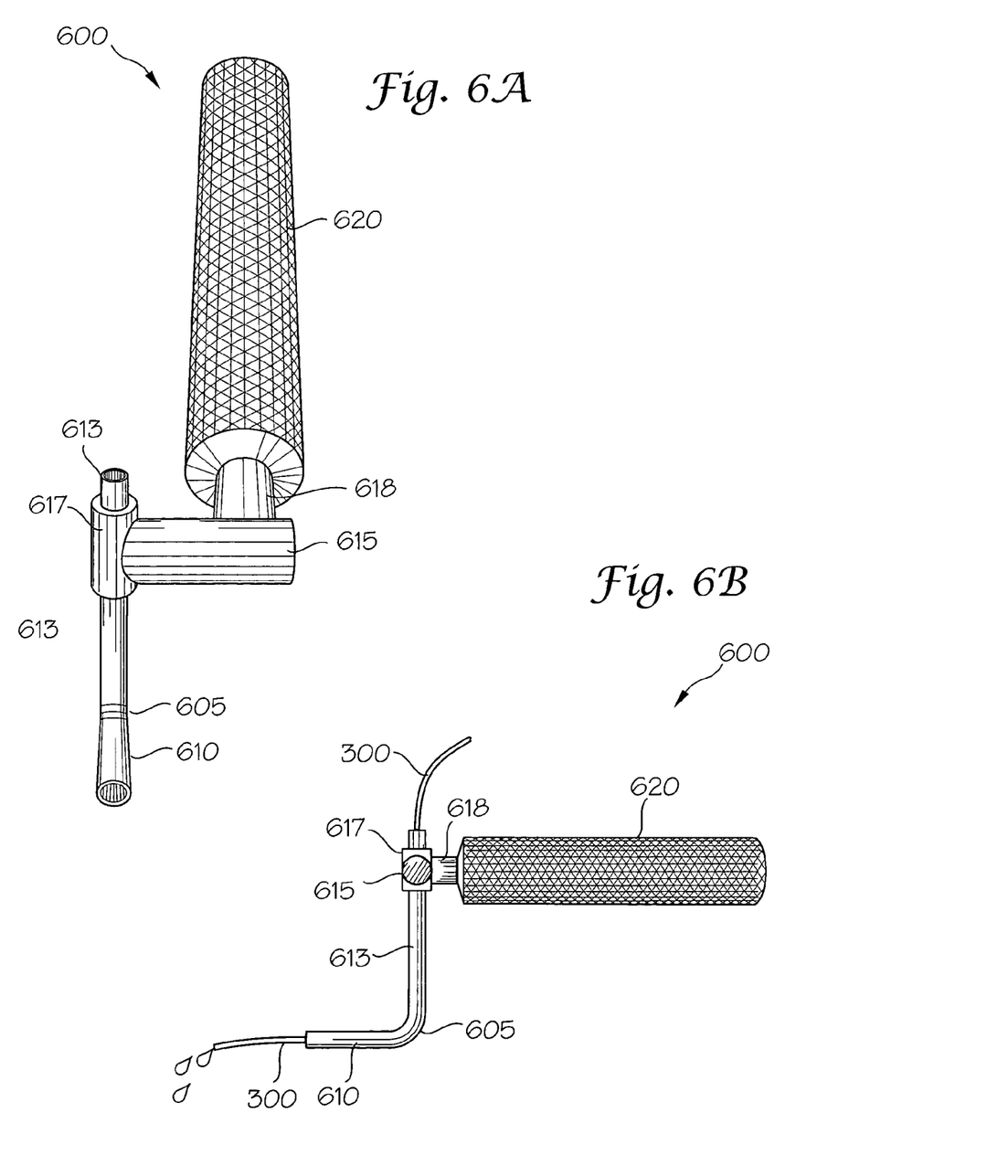
FIG. 6A shows a front perspective view.
FIG. 6B shows a side view of said embodiment.

FIGS. 6(A,B) shows an alternative embodiment of the subject invention directed to a catheter placement apparatus 600. The apparatus 600 comprises a guide conduit 605 that comprises an elongated portion 613 and a delivery arm portion 610. At a position along the elongated body portion 613, an extending member 615 is engaged to the elongated body portion 613 by a bracket 617. A handle 620 is attached to the extending member 615, preferably via an interlink member 618. FIG. 6B shows a side view of the apparatus embodiment 600 shown in FIG. 6A with a catheter 300 inserted into the guide conduit 605. The apparatus embodiment 600 is preferably configured such that the handle 620 is aligned in a parallel linear relationship to the delivery arm portion 610. This assists the surgeon in proper alignment of the guide conduit 605 in the surgical site and proper placement of the catheter 300.

Figures 7A, 7B:
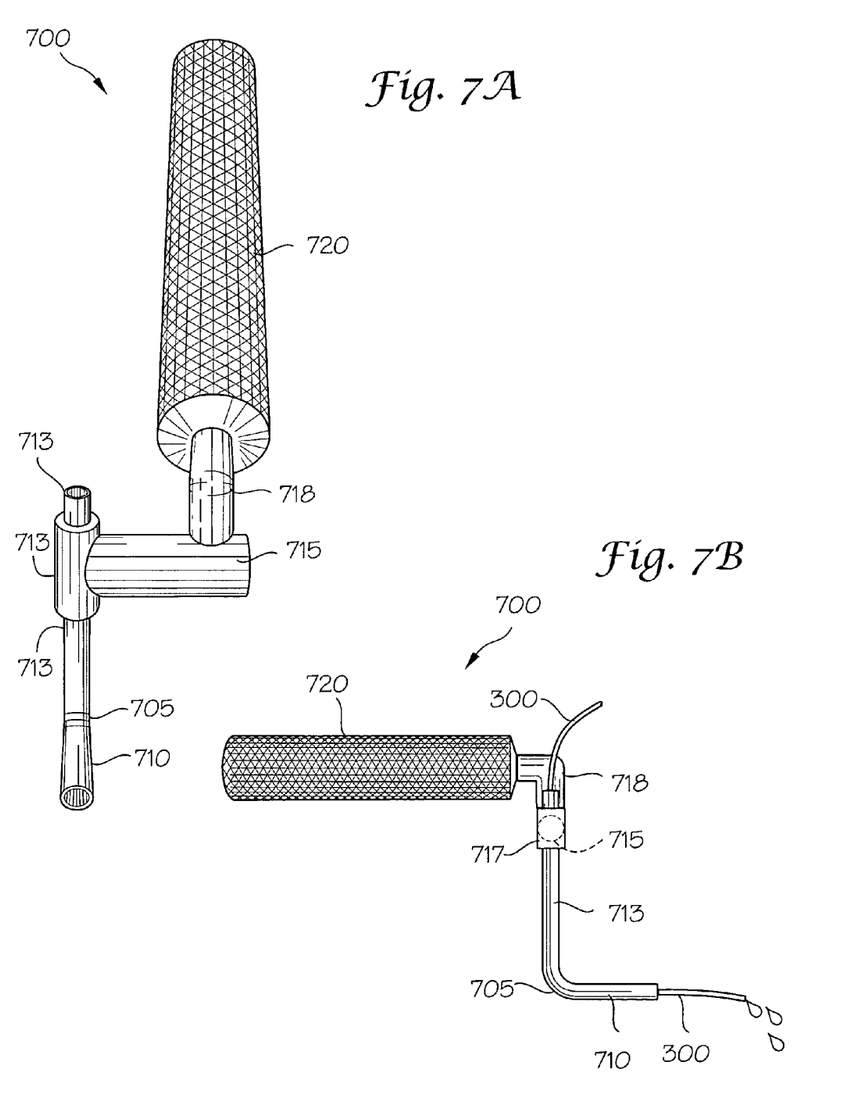
FIG. 7A shows a front perspective view.
FIG. 7B shows a side view of said embodiment.

FIGS. 7(A,B) shows an alternative embodiment of the subject invention directed to a catheter placement apparatus 700. The apparatus 700 comprises a guide conduit 705 that comprises an elongated portion 713 and a delivery arm portion 710. At a position along the elongated body portion 713 an extending member 715 is engaged to the elongated body portion 713 by a bracket 717. A handle 720 is attached to the extending member 715, preferably via an interlink member 718 which bends and extends backward in a substantially L-shaped manner. This feature of the interlink member 718 may provide further clearance out of the surgical site thereby providing increased maneuverability for the apparatus 700. FIG. 7B shows a side view of the apparatus embodiment 700 shown in FIG. 7A with a catheter 700 inserted into the guide conduit 705. The apparatus embodiment 700 is preferably configured such that the handle 720 is aligned such that its longitudinal axis and the longitudinal axis of the delivery arm 710 are disposed in respective parallel plants. This assists the surgeon in proper alignment of the guide conduit 705 in the surgical site and proper placement of the catheter 700.

Figures 8A, 8B:
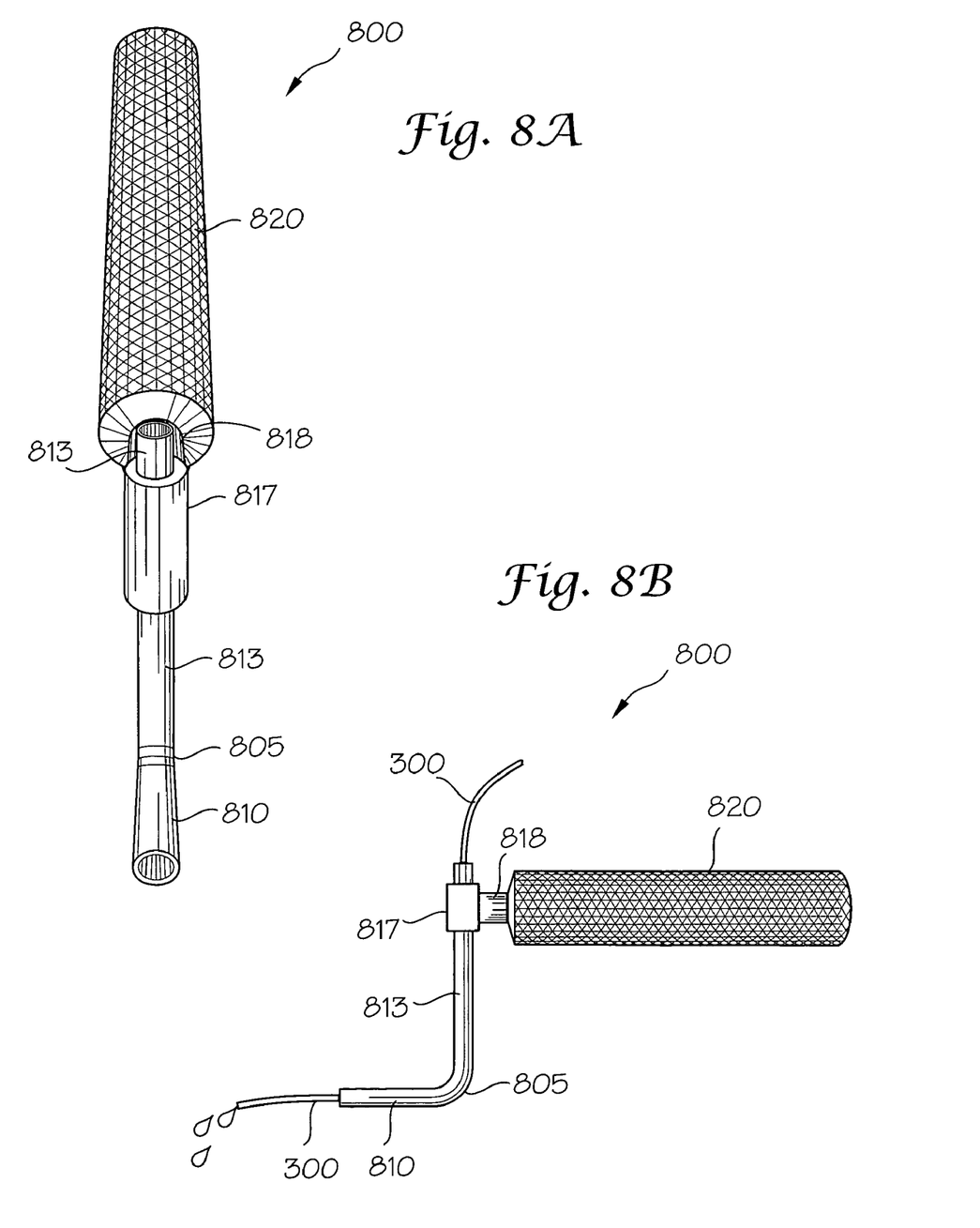
FIG. 8A shows a front perspective view.
FIG. 8B shows a side view of said embodiment.

FIGS. 8 (A,B) shows a catheter placement apparatus similar to that shown in FIGS. 6 and 7 except that catheter placement apparatus 800 lacks an extender member portion. The apparatus 800 comprises a guide conduit 805 that comprises an elongated portion 813 and a delivery arm portion 810. At a position along the elongated body portion 813 an extending member 815 is engaged to the elongated body portion 813 by a bracket 817. FIG. 8B shows a side view of the apparatus embodiment 800 shown in FIG. 8A with a catheter 800 inserted into the guide conduit 805. As noted, the handle 820 attaches directly to the guide conduit 805 and is thus configured such that the handle 820 is aligned in a direct coplanar relationship to the delivery arm portion 810. This configuration may, in certain instances, provide increased accuracy with respect to the alignment of the guide conduit 805 in the surgical site and proper placement of the catheter 800.

Figures 9, 10:
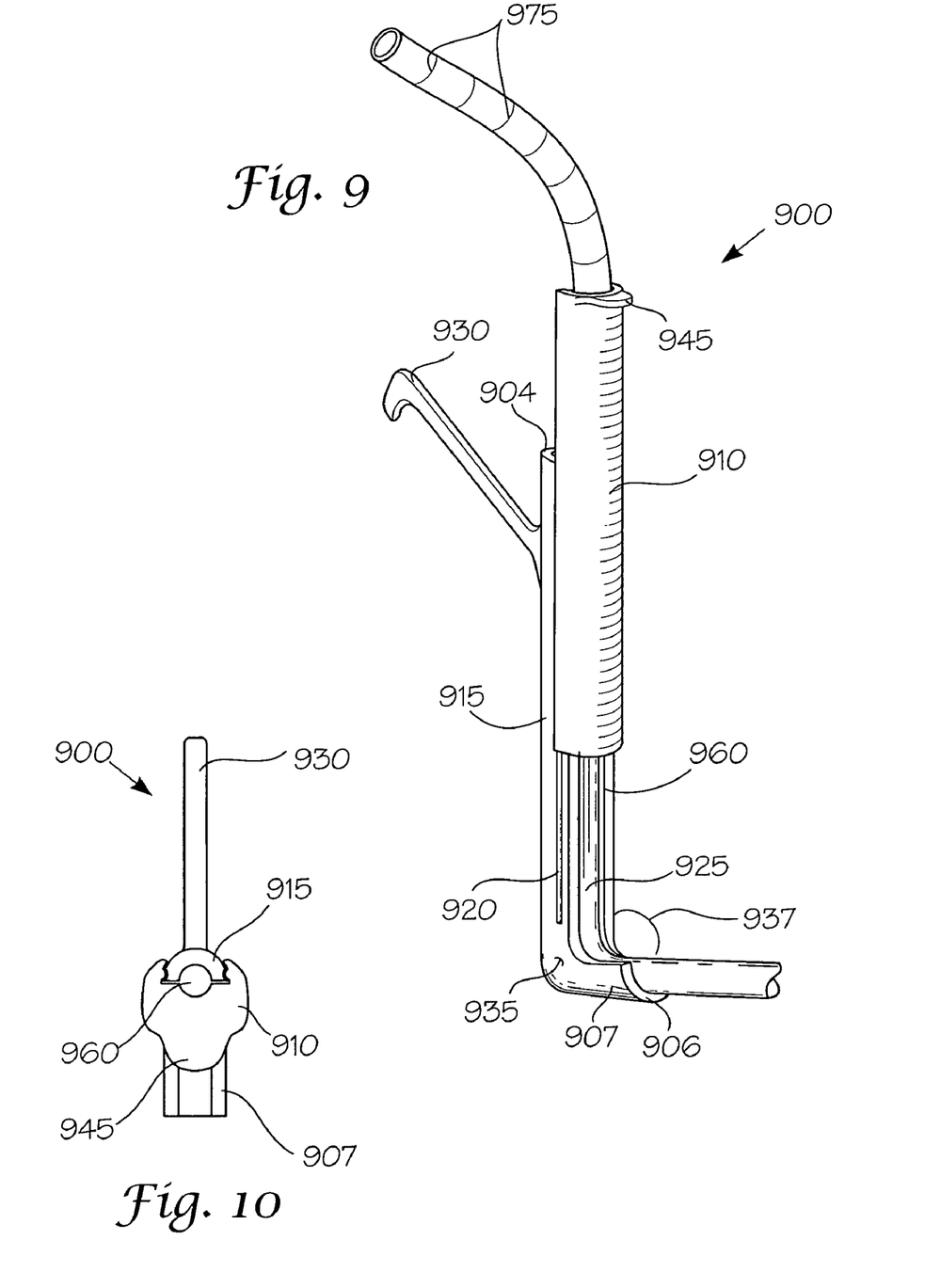
FIG. 9 shows a perspective view of a catheter placement apparatus embodiment comprising a first and second part removably attachable to each other.
FIG. 10 shows a top view of the apparatus embodiment shown in FIG. 9.

FIGS. 9–10 show a perspective view and top view, respectively, of a catheter placement apparatus 900 comprising a guide conduit 903 having a proximal end 904 and a distal end 906. The guide conduit 903 comprises an elongated portion 905 and a delivery arm portion 907 with a bend 935 forming the transition between the elongated portion 905 to the delivery arm portion 907. The delivery arm portion 907 may be from about 0.2 cm to about 5 cm in length and said elongated body portion is from about 1 cm to about 10 cm in length. In a particular embodiment, the delivery arm portion is 0.5 to 1.5 cm in length. The length of the delivery arm portion 907 is not critical so long as it works to direct the distal end of a catheter to the desired target site. The bend 935 comprises an angle 937, which may between about 30 to about 120 degrees. In one embodiment, angle 937 is less than 90 degrees. In another embodiment, angle 937 is between about 70 degrees and 89 degrees. The elongated portion comprises a first conduit component 910 that is slidingly attachable to a second conduit component 915. Those skilled in the art will appreciate that the features of the first and second components 910, 915 that enable a sliding engagement between them is not critical so long as such sliding engagement is achieved. In a alternate version, the first component 910 comprises a ridge that slides in groove defined on the second component 915, or vice versa. Further, those skilled in the art will appreciate other configurations of first and second components that will achieve the removable engagement between them, including, but not limited to, a clip mechanism, friction fitting sliding mechanism, snap fit mechanism or a tearing or breaking mechanism. In another embodiment, the first and second components are removably engageable via a pivoting mechanism whereby the substantially enclosed channel opens up.

A catheter 925 fits through the channel 960 of the guide conduit. The dimensions of the channel are configured to receive and direct a catheter of a predetermined diameter. Attached to or integrated with the second component 915 is a handle 930 and finger rest 945 to assist in manipulation of the apparatus 900 in the surgical site.

The catheter used in conjunction with embodiments described herein may have disposed thereon markings disposed thereon to assist the user in determining the proper placement of the catheter to the target site. See FIG. 9, item 975. For example, the catheter may have marks in the such as, but not limited to, lines or notches that are disposed on the catheter at intervals predetermined to correlate with the extent the catheter extends out of the distal end of the guide conduit to the target site. The placing and spacing of the marking may be adjusted according to considerations such as the dimensions of the guide conduit, the desired distance for the catheter to travel, etc. For example, a first marking may be disposed indicating when the distal tip of the catheter is even with the distal tip of the guide conduit. From there, markings may be spaced in even increments, such as, but not limited to 5, 6, 7, 8, 9, 10, 11, 12, 13, 14, or 15 mm (or other unit of measure) increments, or may be spaced to indicate a predetermined distance from the distal tip of the guide conduit.

Figure 11:
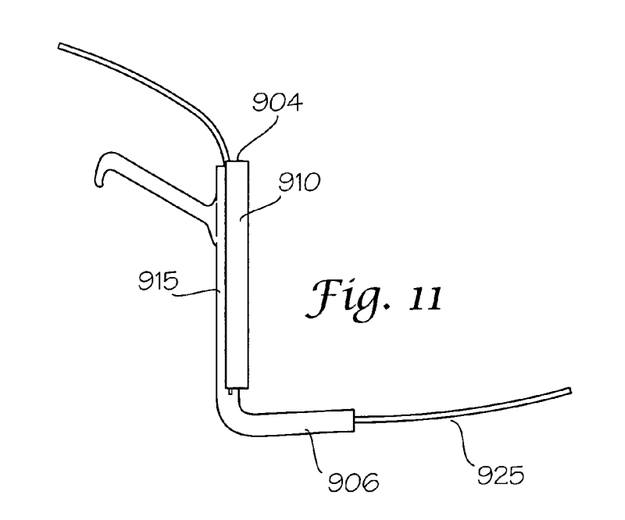
FIGS. 11–13 show side views of the apparatus embodiment shown in FIG. 9 depicting the removably attachable feature of the apparatus embodiment.
Figures 12, 13:
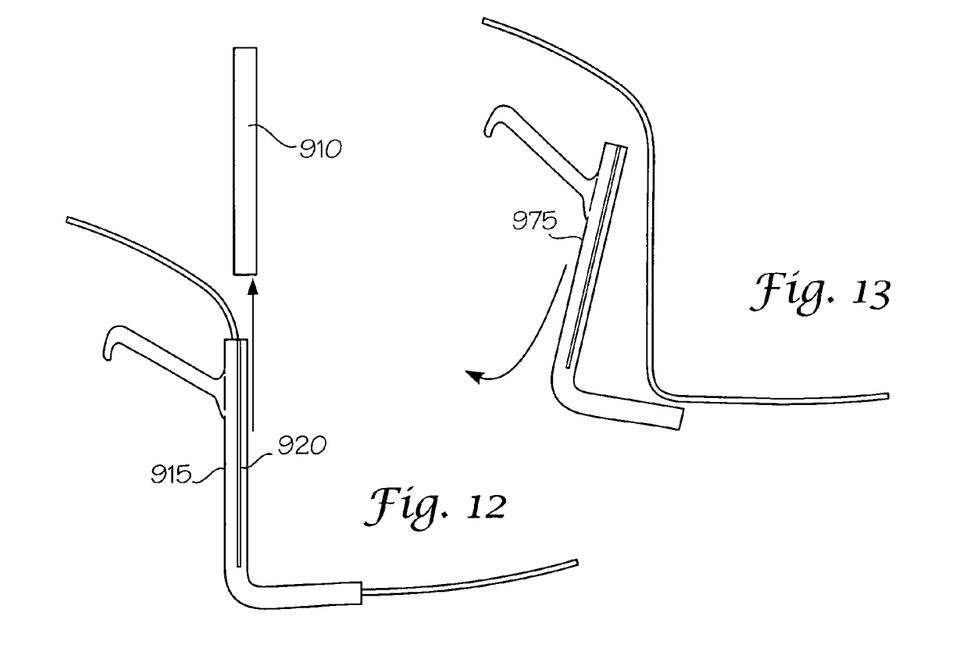

FIGS. 11–13 are side views of the apparatus 900 shown in FIGS. 9 and 10 that depict the basic use of the apparatus 900 and facilitation of the removal of the apparatus 900 from the catheter 925. The apparatus 900 is placed in the surgical site and catheter is directed into the guide conduit 903 (having first and second components 910,915, respectively) at the proximal end 904 and through the conduit 903 such that the catheter 925 extends out the distal end 906 toward the target site. After catheter 925 is in place, first component 910 is slidingly removed from the second component 915. See FIG. 12. With first component 910 removed, the second component may be tilted away and/or pushed back away from the catheter 925 and removed from the surgical site without disrupting the placement of the catheter 925. See FIG. 13.

It should be noted that the delivery arm portion of the guide conduit may be of any desired length depending on the desired use guide conduit and effectiveness. For example, the delivery arm portion may comprise a very short tab serving as a deflector to direct the catheter at a transverse angle to the elongated body portion.

EXAMPLE 1

Intraoperative Administration of Analgesia

1) A Kerrison punch is used to expose the midline fat pad if necessary from the surgical bone exposure of the epidural space used in the decompression surgery. The placement can be done from either the left or right side in a unilateral surgical procedure or direct midline in a bilateral surgical approach. An angled ball tip probe or Woodson probe is used to start the initial path of the catheter and guide.

2) The right angle guide conduit is inserted with the distal end of the conduit pointing cephalad in the dorsal midline.

3) Initial metal stylet wire with ball tip is inserted to "clear a path" for the injection catheter. This can be advanced a few millimeters to a few centimeters.

4) Insertion of the catheter with guide wire through the conduit with the distal tip threaded 3 to 5 inches above the surgical site (to the anatomic bony lecvel of L1 to T10). Note that the surgical site may be at any appropriate location along the spine, but typically, surgical site is at the L4-L5 or L5-S1 level and occasionally the L3-L4 level)

5) The guide conduit is then removed leaving the catheter in place.

6) The distal end of the catheter has the Luer-Lok connector connected and the syringe with anesthetic agents is connected to form a closed system.

7) Wound is closed in the usual manner to the subcutaneous layer. The injection of the epidural analgesia is now performed just before completing the subcutaneous closure and the anesthesiologist records this inject in the operative record. The surgeon dictates in the operative report the placement of the epidural catheter, the injection of the anesthetic agent "to aid in post operative analgesia" and then uses a separate bill code for this injection as appropriate.

8) The skin layer is injected with Sensorcaine and skin closer is completed. The patient should wake up incisional pain free and comfortable. Some patients comment on the new sore throat condition that occurs from the mechanical irritation of the intubation as this is not covered by the epidural analgesia. Post operative pain management typically involves a Fentanyl patch or oral narcotics in addition to any NSAID utilized by the patient preoperatively. The recovery room nursing staff is alerted to the epidural injection and are monitoring the "dizziness or light headedness" of the patient as the epidural injection can interfere cause some orthostatic hypotension and in rare cases some motor weakness in the legs in the first hour. When these drug related clinical signs resolve the patient is ambulated and discharged.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of any patents and other references cited herein are incorporated herein by reference to the extent they are not inconsistent with the teachings herein.

What is claimed is:

1. An apparatus for assisting placement of a catheter in a surgical procedure, said apparatus comprising:
- a guide conduit comprising an elongated portion and a delivery arm portion integrated with or attached to said elongated portion, wherein said guide conduit defines a substantially enclosed channel;
- an extender attached to or integrated with said guide conduit; and
- a handle attached to or integrated with said extender, wherein said handle and said delivery arm portion are positioned such that a longitudinal axis of said handle and a longitudinal axis of said delivery arm portion are disposed in respective parallel planes;
- wherein said handle is attached to or integrated with said extender via an interlink member.

2. An apparatus for positioning a catheter for delivering analgesia to a target site during a surgical procedure, the apparatus comprising:
- a first component comprising a finger rest proximate a proximal end and an elongated section extending from the proximal end;
- a second component comprising a handle proximate a proximal end, an elongated section extending away from the proximal end to a bend region, and a delivery arm portion extending from the bend region toward a distal end, the respective elongated sections of the first and second components cooperating to define a channel for receiving a catheter when the first and second components are engaged; and
- a means for removable engagement between the first and second components;
- wherein the means for removable engagement comprises a ridge formed on a first of the first and second components and a groove formed on a second of the first and second components, the ridge and groove cooperating to engage the first and second components and slidingly separable for separating the first and second components for release of the catheter from the channel.

3. The apparatus of claim 2, wherein the bend region defines an angle of between about 30 to about 120 degrees.

4. The apparatus of claim 2, wherein the bend region defines an angle of less than 90 degrees.

5. The apparatus of claim 2, wherein the bend region defines an angle of between about 70 and 89 degrees.

* * * * *